(12) United States Patent
DeVeaux (10) Patent No.: US 9,913,697 B1
(45) Date of Patent: Mar. 13, 2018

(54) PORTABLE WORKSTATION FOR HEALTHCARE PROFESSIONALS

(71) Applicant: Eric A. DeVeaux, Ewing, NJ (US)

(72) Inventor: Eric A. DeVeaux, Ewing, NJ (US)

(*) Notice: Subject to any disclaimer, the term of this patent is extended or adjusted under 35 U.S.C. 154(b) by 0 days.

(21) Appl. No.: 15/338,442

(22) Filed: Oct. 30, 2016

(51) Int. Cl.
  *A61B 50/30* (2016.01)
  *A61B 50/33* (2016.01)
  *A61B 50/18* (2016.01)

(52) U.S. Cl.
  CPC .............. *A61B 50/30* (2016.02); *A61B 50/18* (2016.02); *A61B 50/33* (2016.02)

(58) Field of Classification Search
  None
  See application file for complete search history.

(56) References Cited

U.S. PATENT DOCUMENTS

| | | | |
|---|---|---|---|
| 1,081,221 A | 12/1913 | Durkin | |
| 3,156,510 A | 11/1964 | Hindin et al. | |
| 3,936,109 A * | 2/1976 | Richardson | A47B 19/08 108/150 |
| 4,073,240 A | 2/1978 | Fly | |
| 4,436,353 A * | 3/1984 | Tucker | A45F 4/00 190/11 |
| 4,558,847 A * | 12/1985 | Coates | A61D 3/00 254/122 |
| 4,927,214 A | 5/1990 | Kaufman et al. | |
| 4,982,820 A | 1/1991 | Scott | |
| 5,375,276 A * | 12/1994 | Nelson | A61G 1/06 5/503.1 |
| 5,660,117 A * | 8/1997 | Noble | A47B 23/043 108/35 |
| 5,961,134 A * | 10/1999 | Congleton | G06F 1/1628 280/37 |
| 6,227,397 B1 * | 5/2001 | Kim | B65D 88/005 220/1.5 |
| 6,371,495 B2 | 4/2002 | Thompson | |
| 6,578,708 B2 * | 6/2003 | Barnett | A45C 13/02 190/1 |
| 6,634,668 B2 * | 10/2003 | Urffer, III | A47F 5/108 280/47.35 |
| 6,779,466 B2 * | 8/2004 | Shabram, Jr. | A47B 3/0912 108/115 |
| 6,811,006 B1 * | 11/2004 | Mundle | A45C 13/02 190/1 |

(Continued)

OTHER PUBLICATIONS

US 270,588, 09/1983, Kemple (withdrawn).

*Primary Examiner* — John D Walters
*Assistant Examiner* — Hilary L Johns
(74) *Attorney, Agent, or Firm* — LaMorte & Associates P.C.

(57) ABSTRACT

A workstation assembly that can be collapsed into a portable container. The portable container has a first section and second section that can be selectively joined and separated. A lift mechanism is provided that interconnects the first section and the second section. The lift mechanism has an extended configuration and a compressed configuration. When in its extended configuration, the lift mechanism separates the first section from the second section of the portable container by a selected distance. Conversely, when in its compressed configuration, the lift mechanism causes the first section to abut against the second section along a common seam. Wheels are connected to the portable container so that the portable container can roll. A handle is also connected to the container for pulling the container on wheels.

19 Claims, 8 Drawing Sheets

(56) References Cited

U.S. PATENT DOCUMENTS

| | | | | |
|---|---|---|---|---|
| 7,086,510 B2* | 8/2006 | Smith | ................ | A45C 7/0022 |
| | | | | 190/103 |
| 7,252,302 B1* | 8/2007 | Thurn | .................... | B62B 3/027 |
| | | | | 280/47.34 |
| 7,584,830 B2* | 9/2009 | Smith | .................... | A45C 5/14 |
| | | | | 190/11 |
| 7,819,247 B2* | 10/2010 | Gonzalez | ................ | A45C 9/00 |
| | | | | 190/11 |
| 7,870,937 B1* | 1/2011 | Arnao | .................... | A45C 9/00 |
| | | | | 190/1 |
| 8,333,271 B2 | 12/2012 | Gibson | | |
| 8,348,301 B2* | 1/2013 | Darling, III | ........... | A61G 1/013 |
| | | | | 280/640 |
| 8,689,704 B2 | 4/2014 | Hodges et al. | | |
| 8,752,488 B2 | 6/2014 | Moller | | |
| 2002/0023811 A1* | 2/2002 | Silvano | .................... | A45C 3/02 |
| | | | | 190/11 |
| 2004/0226791 A1* | 11/2004 | Levy | ........................ | A45C 9/00 |
| | | | | 190/11 |
| 2007/0028812 A1* | 2/2007 | Dumond | ................ | A47B 3/087 |
| | | | | 108/36 |
| 2007/0278058 A1 | 12/2007 | Angel | | |
| 2009/0212670 A1* | 8/2009 | Bustle | ................ | A47B 21/0314 |
| | | | | 312/209 |
| 2010/0263977 A1 | 10/2010 | Wu | | |
| 2011/0017563 A1* | 1/2011 | Azirian | .................... | A45C 9/00 |
| | | | | 190/11 |
| 2014/0027225 A1* | 1/2014 | Richards | ............. | A45C 7/0031 |
| | | | | 190/13 R |

* cited by examiner

PORTABLE WORKSTATION FOR HEALTHCARE PROFESSIONALS

BACKGROUND OF THE INVENTION

1. Field of the Invention

In general, the present invention relates to work stations that are used by healthcare professionals, such as nurses and physicians. More particularly, the present invention relates to portable work stations that transport and hold the equipment of a specialized healthcare provider, such as an anesthesiologist, wherein the work station is usable both inside and outside of a clean environment.

2. Prior Art Description

Many healthcare providers have specialties and use equipment unique to that specialty. For example, a nurse who collects blood samples has equipment directed to that task. Likewise, an anesthesiologist uses gas masks, gas controls and gas flow detection equipment that is unique to that profession.

Although many specialized health care professionals use specialized equipment, each healthcare provider usually has preferences as to equipment brands and models to be used. Furthermore, each healthcare professional also has preferences regarding where the equipment is positioned and how the equipment is configured during a medical procedure. It is for these reasons and others, that many medical professionals prepare their own workstations prior to conducting a medical procedure. In this manner, the work station can be arranged with the exact equipment and configuration desired by the healthcare professional. The familiarity with the layout of the equipment and the type of equipment at the workstation makes it less likely that a healthcare professional will make an error during the medical procedure.

The problem with having a healthcare professional arrange their own workstation is that many modern healthcare professionals practice their profession in more than one location. For instance, an anesthesiologist may have one procedure in a hospital operating room and another in an outpatient clinic. As such, the healthcare practitioner must either carry their own equipment or arrange existing in-house equipment at multiple locations.

Using a portable workstation solves a lot of problems for a modern healthcare professional. However, it also creates other problems if the healthcare professional sometimes works in a sterile environment, such as an operating room. In the operating rooms of hospitals and surgical centers, the table and stands made available as workstations are traditionally made of stainless-steel. This enables the tables and stands to be periodically sterilized. Operating room sterilization protocols require that medical instruments and supplies, as well as work surfaces of the table itself, be sterilized prior to use.

Many hospital regulations also require routine sterilization of all sections of medical tables used in surgery that are thirty inches or more above the floor. The Centers For Disease Control and various other medical organizations also recommend the routine sterilization of medical instruments, examination tables, and other medical equipment. Most prior art tables and workstations are not easily disassembled for sterilization. Rather, the sterilization requirements are typically met by laying a sterilized disposable drape (cover) on the table prior to the start of a medical procedure and then disposing of the drape after the procedure is completed.

Conventional surgical tables are typically made from stainless steel and are too bulky to be considered portable. Such tables typically have one or more shelves. The edges of the shelves and other parts of the tables are typically rounded to avoid snagging or tearing a sterilized disposable surgical drape that is laid over the table. The shelves are structured to hold instruments, trays and baskets, packaged medical supplies, and other health care products. To provide mobility, such tables are commonly equipped with an antistatic wheel at each bottom corner. Such prior art tables are exemplified by U.S. Pat. No. 8,689,704 and U.S. Pat. D270,588.

If a portable table or workstation is to be brought into an operating room, it must be properly prepared. This is typically accomplished by cleaning the surgical table using a hand-scrubbing method and/or an ultrasonic cleaning method. Once the table is cleaned, the nurse covers the table with a sterilized disposable surgical drape. After the drape has been properly positioned, a healthcare professional cannot reach under the drape to access a tool or accessory. All tools and accessories must be placed atop the drape. Only previously sterilized medical instruments and/or supplies are placed upon the surgical drape. Accordingly, bringing a protable workstation into a clean environment is little more efficient than simply using the workstation in the sterile environment.

A need therefore exists for a portable workstation that can be easily transported from place-to-place by a healthcare professional, yet can be easily prepped for use in a sterile operation room. In this manner, a healthcare professional can quickly produce a customized workstation whenever that healthcare professional performs his/her job. This need is met by the present invention as described and claimed below.

SUMMARY OF THE INVENTION

The present invention is a workstation assembly that can be collapsed into a portable container. The portable container has a first section and second section that can be selectively joined and separated.

A lift mechanism is provided that interconnects the first section and the second section. The lift mechanism has an extended configuration and a compressed configuration. When in its extended configuration, the lift mechanism separates the first section from the second section of the portable container by a selected distance. Conversely, when in its compressed configuration, the lift mechanism causes the first section to abut against the second section along a common seam.

Connectors are provided for locking the first section and the second section together along the common seam of the portable container. Wheels are connected to the portable container so that the portable container can roll. A handle is also connected to the container for pulling the container on wheels.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention workstation assembly can be embodied in many ways, the embodiments illustrated show only a few exemplary embodiments. The exemplary embodiments are selected in order to set forth some of the best modes contemplated for the invention. The illustrated embodiments, however, are merely exemplary and should not be considered as limitations when interpreting the scope of the appended claims.

Figure 1:
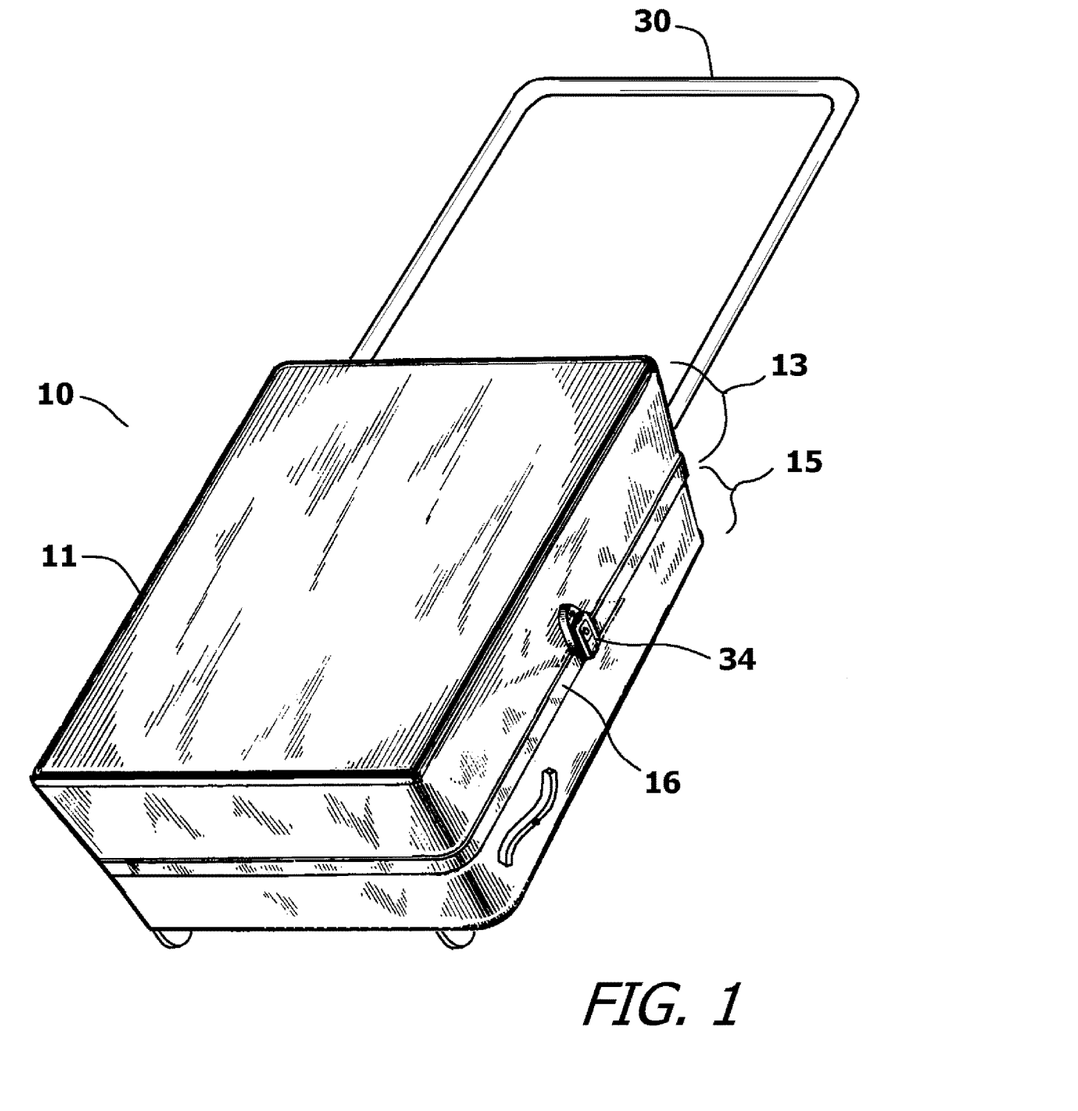
FIG. 1 is a perspective view of a first exemplary embodiment of a workstation assembly in a closed configuration.
Figure 2:
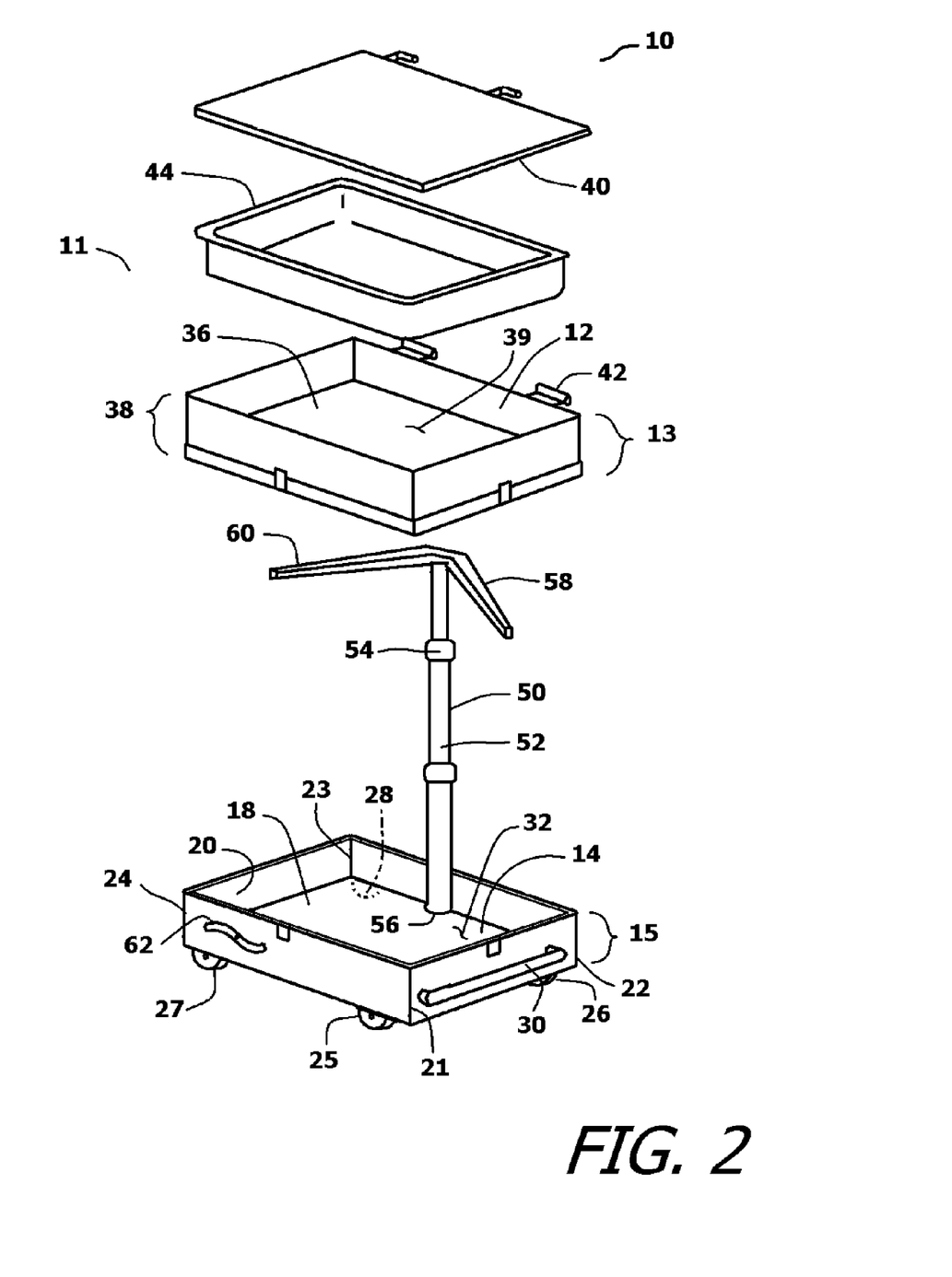
FIG. 2 is an exploded perspective view of the workstation assembly of FIG. 1.

Referring to FIG. 1 and FIG. 2, a workstation assembly 10 is shown. The workstation assembly 10 is configurable as a portable container 11 in which equipment can be stored and transported. In FIG. 1, the portable container 11 is shown in a closed configuration. In the closed configuration, the portable container 11 has the shape and appearance of a piece of wheeled luggage. Accordingly, the portable container 11 can be carried, rolled and otherwise transported in the same manner as a piece of wheeled luggage. The portable container 11 has two sections. The first section 13 defines a primary compartment 12. The second section 15 defines a secondary compartment 14. The first section 13 and the second section 15 are stacked together and joined along a common peripheral seam 16. The first section 13 is stacked atop the second section 15. The second section 15, therefore, serves as the base for the workstation assembly 10. In the second section 15, a secondary compartment 14 is provided that is box shaped. The secondary compartment 14 is defined by a base panel 18 with upwardly extending peripheral walls 20 that meet at four corners 21, 22, 23, 24. Wheels 25, 26, 27, 28 are attached to the second section 15 at the four corners 21, 22, 23, 24. The wheels 25, 26, 27, 28 support the second section 15 above the ground, wherein the all the wheels 25, 26, 27, 28 touch the underlying surface when the base panel 18 is parallel to the ground. In the shown embodiment, the wheels 25, 26, 27, 28 are fixed. However, it should be understood that caster wheels and/or retractable wheels can be used in place of the fixed wheels 25, 26, 27, 28.

A retractable handle 30 is provided. The retractable handle 30 extends from the second section 15 along the base panel 18. The retractable handle 30 enables the workstation assembly 10, when closed, closed to be tilted and pulled for transport. When tilted by the retractable handle 30, the workstation assembly 10 rolls upon two of the wheels 25, 26 in the same manner as a traditional piece of wheeled luggage. Although not shown, it will be understood that one or more carry handles can be affixed to the exterior of the workstation assembly 10 so that the workstation assembly 10 can be carried without use of the retractable handle 30.

The secondary compartment 14 in the second section 15 of the portable container 11 has an open top 32. The open top 32 is completely covered by the presence of the first section 13 of the portable container 11 when the workstation assembly 10 is closed. When stacked atop each other, the first section 13 is closed over the second section 15 by connectors 34 that engage across the peripheral seam 16. When the connectors 34 are open, the first section 13 separates from the second section 15 along the peripheral seam 16.

In the first section 13, the primary compartment 12 has a flat rectangular bottom 36 and four walls 38 that extend upwardly from the periphery of the flat rectangular bottom 36. The primary compartment 12 has an open top 39. The open top 39 is covered by a flat tray panel 40. In the shown embodiment, the flat tray panel 40 is coupled to the first section 13 with a detachable hinge connection 42. In this manner, the flat tray panel 40 can be selectively detached from the first section 13 to provide access to the primary compartment 12, if needed. When attached, the flat tray panel 40 can be rotated about the hinge connection 42 between an open position and a closed position.

The flat tray panel 40 is preferably made of a material, such as stainless steel or polished aluminum, that is easily sanitized in a tray autoclave. In this manner, the tray panel 40 can be separated from the first section 13 and sterilized prior to any procedure in an operating room or other clean environment.

An instrument bin 44 is provided that fits within the primary compartment 12 under the tray panel 40. The instrument bin 44 can be open or can be divided into different sections. Regardless, the instrument bin 44 is also fabricated from a material that is readily sanitized in an autoclave. In this manner, the instrument bin 44 can be removed from the workstation assembly 10 and separately sanitized prior to any procedure in an operating room or other clean environment.

Once the connectors 34 are undone, the first section 13 of the workstation assembly 10 can separated from the second section 15 along the peripheral seam 16. However, the first section 13 and the second section 15 remain interconnected via a lift mechanism 50. The lift mechanism 50 can be any mechanism, device or assembly that can both support and actively elevate the first section 13 of the workstation assembly 10 above the second section 15 of the workstation assembly 10. In the shown embodiment, the lift mechanism 50 is a telescoping shaft 52. The telescoping shaft 52 can be adjusted in height by selectively tightening and/or loosening threaded collars 54 disposed along the telescoping shaft 52. Preferably, the telescoping shaft 52 contains internal springs that bias the telescoping shaft 52 into an extended position. In this manner, when the first section 13 and the second section 15 of the workstation assembly 10 are separated along the peripheral seam 16, the spring bias in the telescoping shaft 52 assists in the raising of the first section 13 above the secondary compartment 15.

Figure 3:
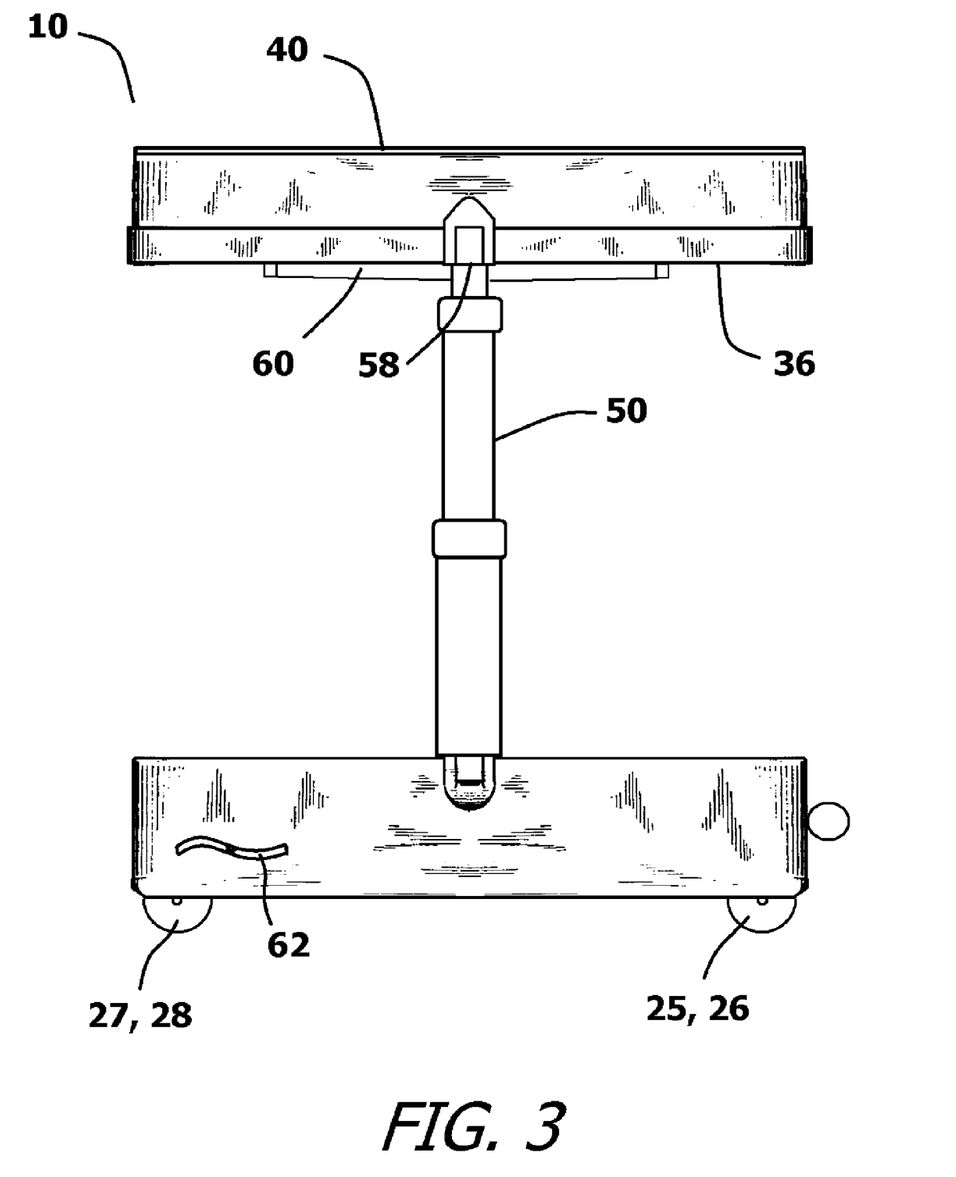
FIG. 3 is a front view of the workstation assembly shown in an open configuration.

Referring to FIG. 3 in conjunction with FIG. 2, it will be understood that since the lift mechanism 50 is adjustable, it will be understood that the tray panel 40 on the top of the primary compartment 12 can be set to any height desired by the healthcare professional using the workstation assembly 10. As such, the workstation assembly 10 can be set at an ergonomically correct position for people of different heights and for people who are sitting or standing.

The lift mechanism 50 has a first end 56 mounted within the secondary compartment 14. The opposite second end 58 of the lift mechanism 50 terminates with a mounting bracket 60. The mounting bracket 60 interconnects with the bottom 36 of the primary compartment 12. It is preferred that the connection between the mounting bracket 60 and the bottom 36 of the primary compartment 12 is not permanent. Rather, it is preferred that with a directed manipulation, the first section 13 can be detached from the mounting bracket 60 for separate use or for cleaning and/or sterilization.

Once a healthcare professional has set the workstation assembly 10 to a desired height, that professional has the option to roll the workstation assembly 10 into different positions. This is easily done since the workstation assembly 10 rests upon its wheels 25, 26, 27, 28 when opened. Conversely, if a healthcare professional does not want the workstation assembly 10 to roll, a wheel lock 62 is provided. The wheel lock 62 is foot operated and locks one or more of the wheels 25, 26, 27, 28 when activated by the foot of the healthcare professional.

Referring to FIG. 1 through FIG. 3, it will be understood that in order to use the workstation assembly 10 in a patient's home, a clinic examination room, or some other unsterile environment, the healthcare professional merely loads his/her equipment and tools into the primary compartment 12 and the secondary compartment 14 of the workstation assembly 10. The workstation assembly 10 is then closed, as is shown in FIG. 1, and transported to any location in the same manner as a piece of wheeled luggage.

Once at a desired location, the workstation assembly 10 is opened. The workstation assembly 10 is rested upon all its wheels 25, 26, 27, 28 to be stable. The first section 13 with its primary compartment 12 is then separated from the second section 15 and its secondary compartment 14 along the peripheral seam 16. The lift mechanism 50 raises the primary compartment 12 above the secondary compartment 14. The primary compartment 12 is raised to a height required by the healthcare professional. The tools and equipment kept within the primary compartment 12 and the secondary compartment 14 can then be placed atop the tray panel 40 for use.

Figure 4:
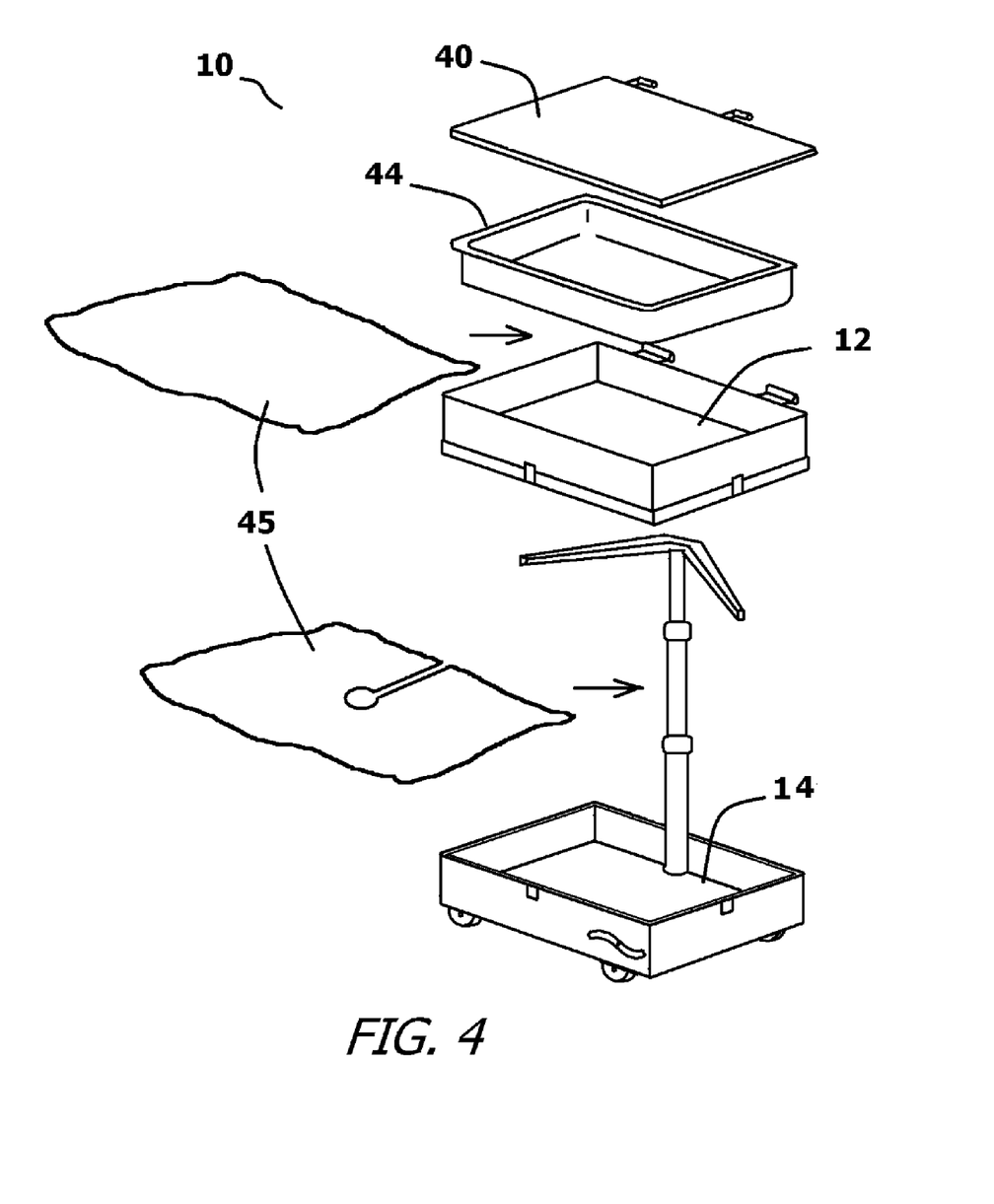
FIG. 4 is an exploded perspective view of the workstation assembly shown with sanitary drapes.
Figure 5:
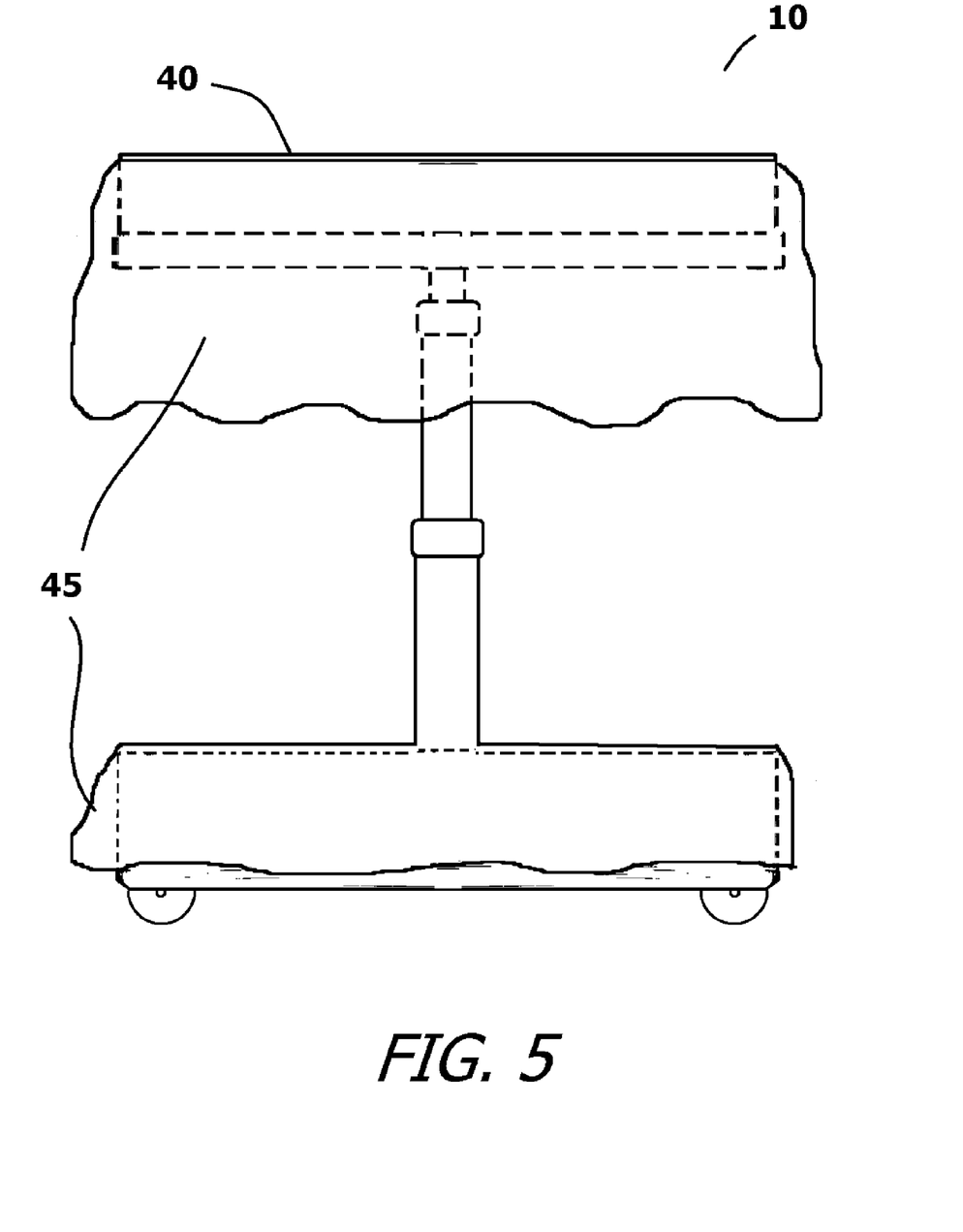
FIG. 5 is a front view of the workstation assembly shown with sanitary drapes.

Referring to FIG. 4 and FIG. 5, it will be understood that the workstation assembly 10 can be readily used in an operating room or similar clean environment with only minor preparations. Prior to use in a clean environment, the workstation assembly 10 is opened and the various equipment and tools removed. The tray panel 40 is also removed, as is the instrument bin 44. All tools are sterilized. The tray panel 40 and instrument bin 44 are also sterilized. The equipment is covered. Prior to returning the cleaned components to the workstation assembly 10, the primary compartment 12 and the secondary compartment 14 are draped with disposable sterile drapes 45. The workstation assembly 10 now complies with CFDC sterilization standards and can be used in a clean environment by the healthcare professional.

Figure 6:
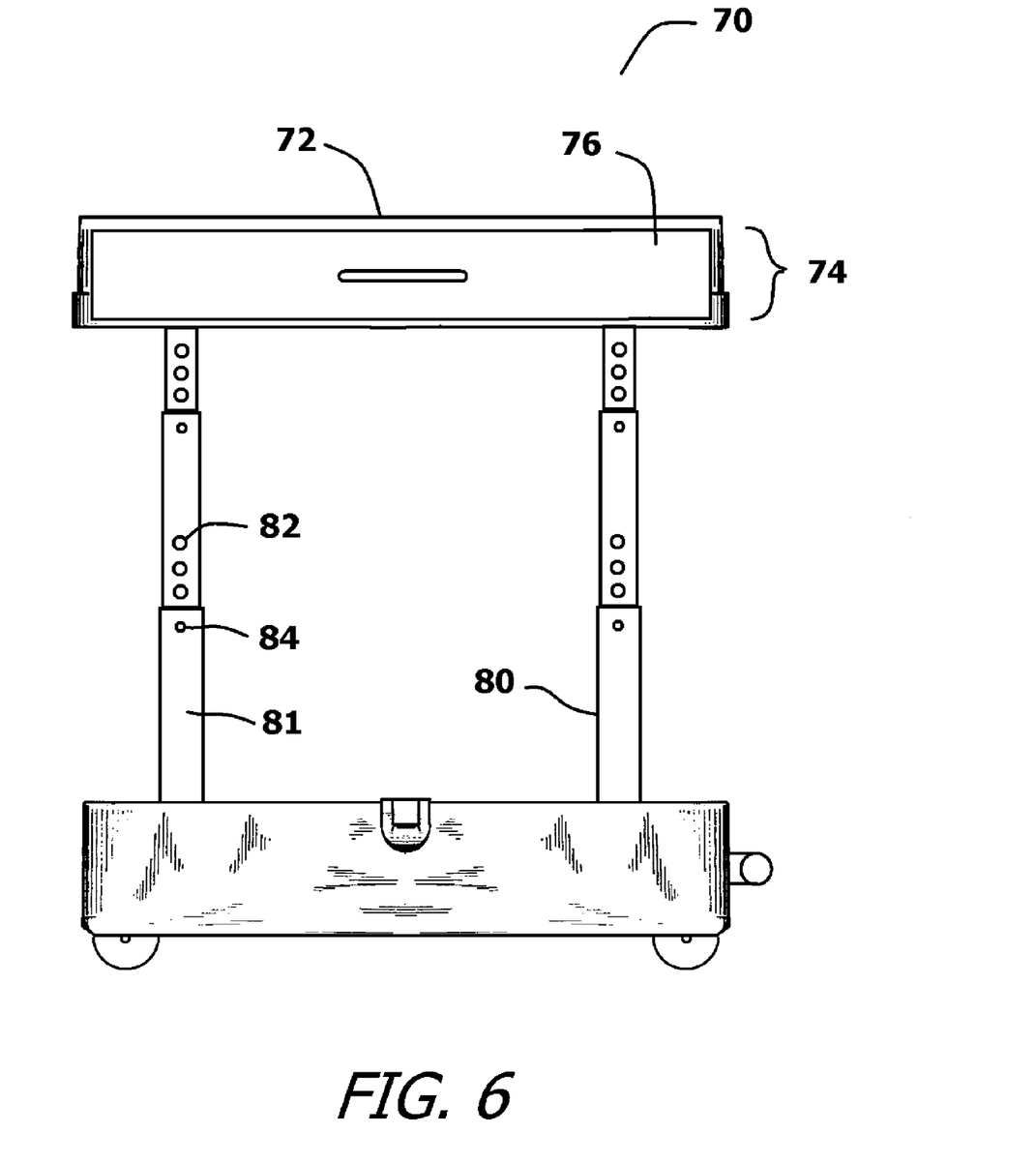
FIG. 6. is front view of an alternate embodiment of a workstation assembly shown in an open configuration.

Referring now to FIG. 6, an alternate embodiment of the workstation assembly 70 is shown. In this embodiment, the tray panel 72 is permanently affixed to the first section 74. However, a drawer 76 is provided that slides into the first section 74. The drawer 76 can be separated from the first section 74 so that each component can be separately sanitized.

In FIG. 6, the lift mechanism 80 is also changed. In this embodiment, the lift mechanism 80 is a telescoping shaft 81 with holes 82 and a locking detent 84. The length of the lift mechanism 80 is altered by which hole 82 along the telescoping shaft 81 is engaged by the locking detents 84.

Figure 7:
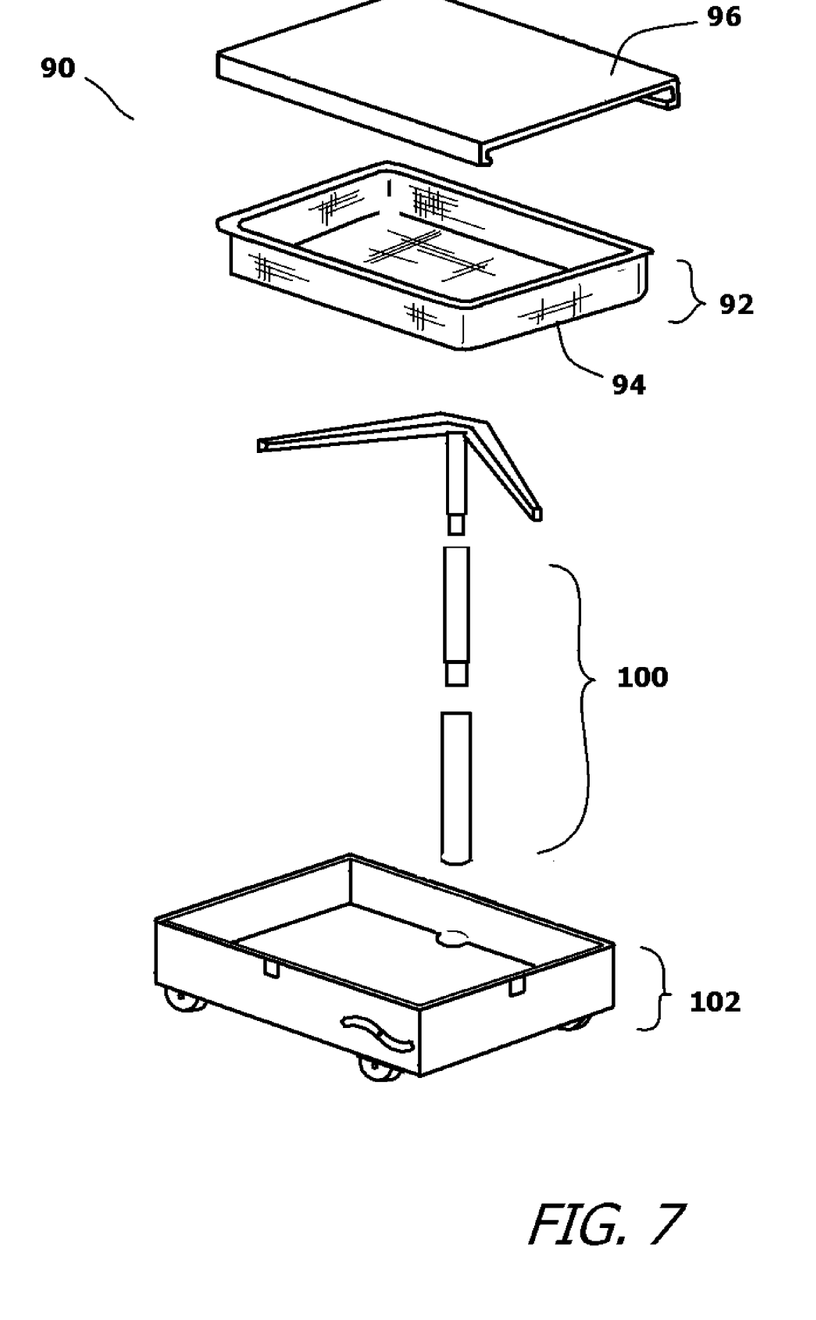
FIG. 7 is an exploded perspective view of an alternate embodiment of a workstation assembly.

Referring now to FIG. 7, a second alternate embodiment of the workstation assembly 90 is shown. In this embodiment, the first section 92 is a basket 94. A tray panel 96 slides onto the basket 94 and can be moved to access the contents of the basket 94. Using the structure of a basket 94 makes the first section 92 easy to sanitize using traditional sanitization protocols.

In FIG. 7, the lift mechanism is replaced with a rigid support structure 100. The rigid support structure 100 can be disassembled from the second section 102 and stored in the second section 102 when not in use. Accordingly, the rigid support structure 100 can be disassembled and sterilized prior to use. This enables a healthcare professional to touch and adjust the rigid support structure 100 without compromising cleanliness protocols.

Figure 8:
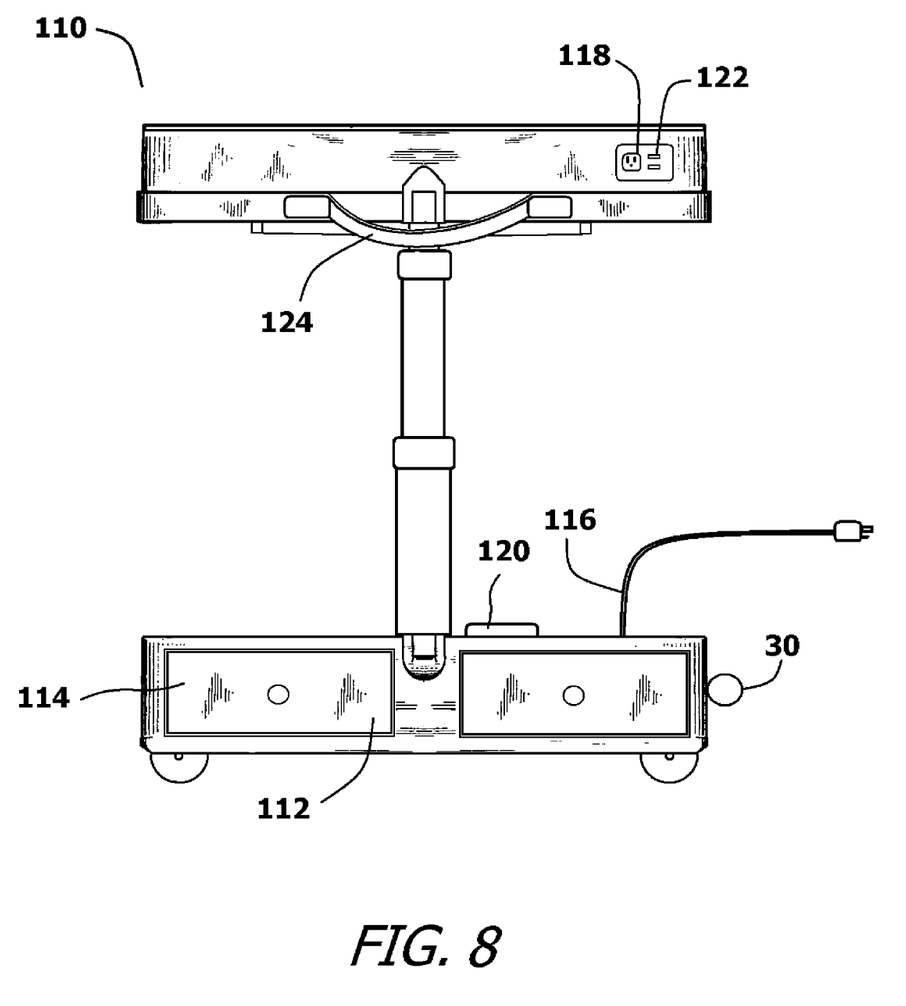
FIG. 8 is a front view of the workstation assembly shown in an open configuration.

Referring now to FIG. 8, an alternate embodiment of the workstation assembly 110 is shown. In this embodiment, draws 112 are built into the second section 114 of the workstation assembly 110. In addition, the workstation assembly 110 is provided with a plug 116. The plug 116 provides power to at least one receptacle 118. The plug 116 may also be used to charge a battery 120. The battery 120 provides DC power and can be used as a power failure backup. It also can be used to power USB ports 122.

In FIG. 8, the workstation assembly 110 is also shown with a carry handle 124. The carry handle 124 can be used to carry and move the workstation assembly 110 when the pull handle 30 is retracted.

It will be understood that the embodiments of the present invention that are illustrated and described are merely exemplary and that a person skilled in the art can make many variations to those embodiments. Furthermore features from the different embodiments can be mixed and matched as a matter of design choice. All such embodiments are intended to be included within the scope of the present invention as defined by the claims.

What is claimed is:

1. A workstation assembly, comprising:
   a portable container having a first section and second section that can be selectively joined and separated;
   a lift mechanism that interconnects said first section and said second section, wherein said lift mechanism has an extended configuration and a compressed configuration, wherein when in said extended configuration, said lift mechanism separates said first section from said second section by a selected distance, and when in said compressed configuration, said lift mechanism causes said first section to abut against said second section along a common seam;
   a tray panel connected to said first section of said container, wherein said tray panel is selectively detachable from said first section of said container;
   connectors for locking said first section and said second section together along said common seam when said first section and said second section abut along said common seam;
   wheels connected to said portable container; and
   a handle connected to said container for pulling said container on said wheels.

2. The assembly according to claim 1, wherein said tray panel is fabricated from a metal that can be readily sterilized.

3. The assembly according to claim 1, wherein said tray panel is affixed to said first section of said container with a detachable hinge connection.

4. The assembly according to claim 1, wherein said second section has a bottom panel that is parallel to said tray panel both when said lift mechanism is in said extended configuration and when said lift mechanism is in said compressed configuration.

5. The assembly according to claim 1, wherein said lift mechanism is biased into said extended configuration.

6. The assembly according to claim 1, wherein said lift mechanism is a single telescoping shaft.

7. The assembly according to claim 1, wherein said first section has a removable drawer.

8. The assembly according to claim 1, wherein said second section has a drawer.

9. The assembly according to claim 1, wherein said lift mechanism is selectively detachable from said first section of said container.

10. The assembly according to claim 9, wherein said lift mechanism is selectively detachable from said second section of said container.

11. A workstation assembly, comprising:
- a portable container having a first section and a second section that can be selectively separated and joined along a common seam;
- a tray panel connected to said first section of said container, wherein said tray panel is selectively detachable from said first section of said container;
- at least one telescoping shaft that interconnects said first section and said second section, wherein said at least one telescoping shaft is selectively adjustable in length to separate said first section from said second section by a selected distance along said common seam;
- connectors for locking said first section and said second section together along said common seam when said portable container is in a closed condition;
- wheels connected to said portable container; and
- a handle connected to said container for pulling said container on said wheels.

12. The assembly according to claim 11, wherein said handle is retractable into said container.

13. The assembly according to claim 12, wherein said tray panel is metal.

14. The assembly according to claim 13, wherein said tray panel is affixed to said first section of said container with a detachable hinge connection.

15. The assembly according to claim 11, wherein said at least one telescoping shaft is biased into an extended configuration.

16. The assembly according to claim 11, wherein said first section has a removable drawer.

17. The assembly according to claim 11, wherein said at least one telescoping shaft is selectively detachable from said first section of said container.

18. The assembly according to claim 11, wherein said at least one telescoping shaft is selectively detachable from said second section of said container.

19. A workstation assembly, comprising:
- a portable container having a first section and second section that can be selectively joined and separated, wherein said first section has a removable drawer;
- a lift mechanism that interconnects said first section and said second section, wherein said lift mechanism has an extended configuration and a compressed configuration, wherein when in said extended configuration, said lift mechanism separates said first section from said second section by a selected distance, and when in said compressed configuration, said lift mechanism causes said first section to abut against said second section along a common seam;
- a tray panel connected to said first section of said container, wherein said tray panel is selectively detachable from said first section of said container;
- connectors for locking said first section and said second section together along said common seam when said first section and said second section abut along said common seam;
- wheels connected to said portable container; and
- a handle connected to said container for pulling said container on said wheels.

* * * * *